US009556215B2

(12) United States Patent
El Hadri et al.

(10) Patent No.: US 9,556,215 B2
(45) Date of Patent: Jan. 31, 2017

(54) SYNTHETIC PENTASACCHARIDES HAVING SHORT HALF-LIFE AND HIGH ACTIVITY

(75) Inventors: Ahmed El Hadri, Morsang sur Orge (FR); Maurice Petitou, Paris (FR)

(73) Assignee: CARBOMIMETICS, Orsay (FR)

(*) Notice: Subject to any disclaimer, the term of this patent is extended or adjusted under 35 U.S.C. 154(b) by 260 days.

(21) Appl. No.: 14/126,776

(22) PCT Filed: Jun. 18, 2012

(86) PCT No.: PCT/EP2012/061592
§ 371 (c)(1),
(2), (4) Date: Jul. 9, 2014

(87) PCT Pub. No.: WO2012/172104
PCT Pub. Date: Dec. 20, 2012

(65) Prior Publication Data
US 2014/0315814 A1    Oct. 23, 2014

(30) Foreign Application Priority Data

Jun. 17, 2011  (EP) .................... 11305765

(51) Int. Cl.
C07H 15/26 (2006.01)
C07H 11/00 (2006.01)
C07H 5/04 (2006.01)
C07H 3/06 (2006.01)
A61K 31/702 (2006.01)
A61K 38/17 (2006.01)

(52) U.S. Cl.
CPC .............. C07H 3/06 (2013.01); A61K 31/702 (2013.01); A61K 38/1709 (2013.01); C07H 5/04 (2013.01); C07H 11/00 (2013.01); C07H 15/26 (2013.01)

(58) Field of Classification Search
None
See application file for complete search history.

(56) References Cited

U.S. PATENT DOCUMENTS

| | | | |
|---|---|---|---|
| 5,543,403 A | 8/1996 | Petitou et al. | |
| 6,174,863 B1 | 1/2001 | van Boeckel et al. | |
| 6,670,338 B1 | 12/2003 | Petitou | |
| 6,844,329 B2 * | 1/2005 | Duchaussoy | A61K 31/715 514/25 |
| 2007/0293442 A1 | 12/2007 | Buijsman et al. | |
| 2010/0081708 A1 * | 4/2010 | Petitou | C07H 11/00 514/44 R |

FOREIGN PATENT DOCUMENTS

| | | |
|---|---|---|
| EP | 1574516 | 9/2005 |
| EP | 1322673 | 9/2007 |
| EP | 2074131 | 7/2009 |
| WO | WO 99/25720 | 5/1999 |
| WO | WO 99/36428 | 7/1999 |
| WO | WO 2006/067173 | 6/2006 |
| WO | WO 2008/041131 | 4/2008 |
| WO | WO 2011/073408 | 6/2011 |

OTHER PUBLICATIONS

Harenberg, Job, Thrombosis Haemostasis, "Development of idraparinux and idrabiotaparinux for anticoagulant therapy", 2009, vol. 102, pp. 811-815.*
Gould: "Salt selection for basic drugs"; ., International Journal of Pharmaceutics, vol. 33, issues 1-3, Nov. 1986, pp. 201-217 (Abstract 2 pages).
Berge et al. :"Pharmaceutical Salt"; Journal of Pharmaceutical Sciences, vol. 66 (1), Jan. 1977, pp. 1-19.
Brill et al.: "Opening of Levoglucosane Derived Epoxides with Oxygen, Nitrogen and Sulfur Nucleophiles"; Tetrahedron Letters, 39 (1998), pp. 787-790.
Gould: "Salt selection for basic drugs"; ., International Journal of Pharmaceutics, vol. 33, issues 1-3, 1984, 33, 201-271 (Abstract 2 pages).

* cited by examiner

Primary Examiner — Layla Berry
Assistant Examiner — Bahar Craigo
(74) Attorney, Agent, or Firm — Hamre, Schumann, Mueller & Larson, P.C.

(57) ABSTRACT

The invention concerns a pentasaccharide compound of formula (I)

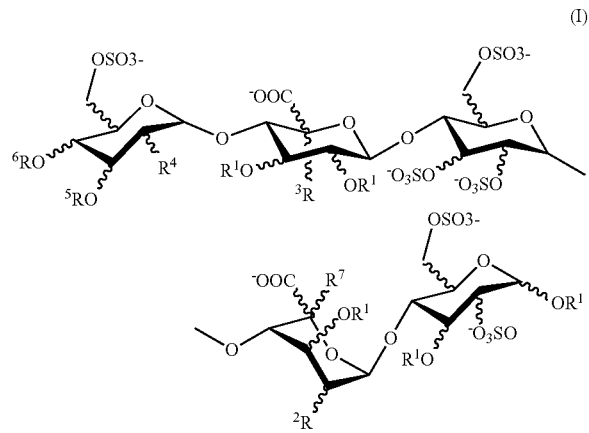

and the salts thereof.
The invention also concerns a pharmaceutical composition comprising the synthetic pentasaccharide compound of formula (I) and its salts. The invention further concerns these compounds for use as a medicament, and in particular intended to treat blood clotting disorders, to prevent ischaemia reperfusion injury associated with solid organ transplantation, or to reduce the risk of blood clotting in an extracorporeal blood circuit during cardiac surgery, extracorporeal membrane oxygenation, or during circulatory assistance such as artificial heart.

11 Claims, No Drawings

SYNTHETIC PENTASACCHARIDES HAVING SHORT HALF-LIFE AND HIGH ACTIVITY

TECHNICAL FIELD

The present invention is concerned with anticoagulants (i.e. substances that prevent blood clotting). More specifically, the present invention is concerned with antithrombotic oligosaccharides.

BACKGROUND ART

Heparin, a natural sulphated polysaccharide, is an anticoagulant that belongs to the family of glycosaminoglycans. The anticoagulant activity of heparin is due to its ability to accelerate the inhibition of several proteases, particularly factor Xa and thrombin, in the blood coagulation cascade.

Heparin and heparin-derived drugs inhibit the activity of factor Xa by attaching to a specific binding domain of antithrombin (AT). Once heparin or heparin-derived drugs are attached to the specific binding domain of antithrombin, they induce a conformational change in antithrombin (AT). This conformational change in AT is responsible for inhibition of factor Xa. Investigations have shown that the lowest structural element capable of significantly binding AT, and inhibiting factor Xa, is a pentasaccharide.

The prototype of such conformational-change-inducing products is fondaparinux. Fondaparinux sodium (Arixtra™—GlaxoSmithKline) is the first of a new class of antithrombotic agents. It displays a half-life in rats of approximately one hour and of 17 h in human. It is given once a day to patients in need of an anticoagulant treatment. It is a chemically synthesised pentasaccharide mimicking the antithrombin binding site of heparin. It is a selective factor Xa inhibitor and thus an inhibitor of thrombin generation.

The synthesis of fondaparinux is long and complicated. Thus, with the aim of simplifying the chemistry while maintaining the same activity and pharmacokinetic profile, new series of pentasaccharides described in U.S. Pat. No. 5,543,403 or in WO 99/36428 have been designed.

U.S. Pat. No. 5,543,403 discloses synthetic pentasaccharides in which N-sulfate, N-acetate and hydroxyl groups are replaced by alkoxy, and O-sulfate groups. WO 99/36428 discloses similar synthetic pentasaccharides, the L-iduronic unit of which is locked in a $^2S_0$ conformation, and the D-glucuronic unit E of which has eventually an ethyl group at position 5.

However, while the presence of alkyl groups on these pentasaccharides unit considerably simplifies their mode of preparation, it also increases the half-life making the clinical use problematic.

EP 2 074 131 also attempts to provide synthetic pentasaccharides. In this application, it was considered that the ability of the pentasaccharides to go through the intestinal barrier was important for an application as antithrombotics.

However, it appeared that many compounds disclosed by EP 2 074 131 also have a too long half-life.

The half-life of anticoagulant pentasaccharides, the time required to halve the plasma concentration of the drug, is a very important pharmacokinetic parameter. Indeed, it is sometimes necessary, e.g. in case of an haemorrhage, to switch off as quickly as possible the anticoagulant effect so that the haemorrhage can be stopped.

Suitable half-lives for an anticoagulant range from about 5 to about 20 hours in human, corresponding to 0.5 hour to about 3 hours in the rat.

Introduction of a biotin moiety on the pentasaccharide allows fast suppression of the anticoagulant activity through injection of avidin, a protein that strongly binds to biotin.

The biotin group (IUPAC name: 5-[(3aS,4S,6aR)-2-oxohexahydro-1H-thieno[3,4-d]imidazol-4-yl]pentanoic acid; also known as vitamin B₇) represents the following group:

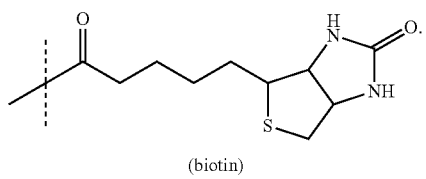

(biotin)

Such biotinylated pentasaccharides are known from EP 1 322 673. Avidin prevents the compounds from having their effect on their targets and accelerates their elimination. The anti-factor Xa activity of the biotinylated compounds of EP 1 322 673 is equivalent to the activity of their non-biotinylated counterparts.

Thus, it is possible to neutralize the anticoagulant activity of biotinylated compounds by administration of avidin which eventually allows using long half-life anticoagulant pentasaccharides.

However, the enzyme biotinidase, that cleaves the amide bond at the carboxylate end of biotin, is present in blood plasma and could react with biotinylated compounds to de-biotinylate them. As a result, the de-biotinylated compounds are no longer neutralised by avidin while keeping their anticoagulant activity until they are physiologically washed out. This is a real problem because anticoagulant treatments can be given for long period of time and the de-biotinylated compound can accumulate in plasma. Therefore, it is still highly desirable to have biotinylated compounds with a short half-life to allow their immediate neutralization in case of emergency and to avoid their accumulation in plasma if they are de-biotinylated by biotinidase.

The authors of the present invention have surprisingly found that the half-life of alkylated/O-sulfated pentasaccharides can be modulated by varying the substituent groups of the D-unit.

Introducing an amino function at position 2 reduces the half-life.

Biotinylation of this 2 amino-function increases the half-life

Introducing one free hydroxyl function at the D-unit reduces the half-life.

A combination of these various observations allowed the authors to identify potent inhibitors of factor Xa biotinylated pentasaccharides with a short half-life.

Thus, one aim of the invention is to provide pentasaccharides, which are easy to synthesize and with a short half-life, and in particular biotinylated pentasaccharides.

Another aim of the invention is to provide biotinylated pentasaccharides with high anti-factor Xa activity, i.e. low value of $IC_{50}$.

Therefore, all drawbacks of the prior art are overcome with the use of the compounds according to the invention, and more in particular the biotinylated ones.

SUMMARY OF THE INVENTION

The invention concerns a synthetic pentasaccharide compound of formula (I)

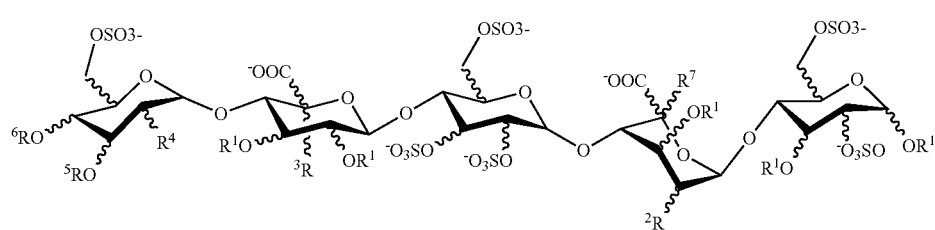

Formula (I)

wherein:
- $R^1$ represents a (C1-C3)alkyl group;
- $R^2$ represents a (C1-C3)alkoxy group and $R^7$ represents a hydrogen atom, or $R^2$ and $R^7$ form a —O—CH$_2$— or a —O—CH$_2$—CH$_2$— bridge, where —O— is linked to the carbon atom bearing the $R^2$ group and —CH$_2$— is linked to the carbon atom bearing the $R^7$ group;
- $R^3$ represents a hydrogen atom or an ethyl group;
- $R^4$ represents —OH, —NH$_2$, or —NH-LC-biotin, wherein LC represents a linker, advantageously of the formula —(C=O)—(CH$_2$)$_n$—NH—, with n from 1 to 10, and more advantageously of formula —(C=O)—(CH$_2$)$_4$—NH;
- when $R^5$ and $R^6$ are different, $R^5$ and $R^6$ are chosen amidst a hydrogen atom, a methyl, an ethyl, a propyl, a butyl and a pentyl group;
- when $R^5$ and $R^6$ are identical, $R^5$ and $R^6$ are chosen amidst a hydrogen atom, a methyl, an ethyl, a propyl and a pentyl group;
- on the proviso that $R^1$ differs from at least one of $R^5$ or $R^6$;
and the salt thereof.

Advantageously the synthetic pentasaccharide compound according to the present invention has the following formula (II)

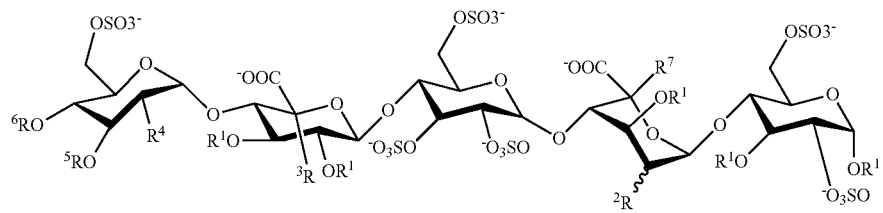

(II)

wherein:

$R^1$, $R^2$, $R^3$, $R^4$, $R^5$ and $R^6$ are as defined above.

R4 may represent —NH$_2$ or —NH-LC-biotin, with LC defined as above.

In one embodiment, $R^5$ and $R^6$ represent the same group.

In another embodiment, one of $R^5$ or $R^6$ represents an hydrogen atom, and the other represents a (C1-C5)alkyl group.

In one variant of all the embodiments described above, $R^2$ and $R^7$ form a —O—CH$_2$— bridge, where —O— is linked to the carbon atom bearing the $R^2$ group and —CH$_2$— is linked to the carbon atom bearing the $R^7$ group, and $R^3$ represents an ethyl group.

In another variant of all the embodiments described above, R2 represents a (C1-C3)alkoxy group, and $R^3$ and $R^7$ represent a hydrogen atoms.

The invention also concerns a pharmaceutical composition comprising the synthetic pentasaccharide compound and salt thereof described hereabove and a pharmaceutically acceptable diluent or carrier.

The invention further concerns the synthetic pentasaccharide compound and salt thereof for use as a medicament, for example intended for the prevention and the treatment of blood clotting disorders.

Blood clotting disorder are, in particular, one of venous thrombosis or arterial thrombosis, including deep vein thrombosis, pulmonary embolism, acute coronary syndromes, myocardial infarction and stroke. Blood clotting disorders may also result from atrial fibrillation.

The invention also concerns the synthetic pentasaccharide compound and salt thereof for use as a medicament for preventing ischaemia reperfusion injury associated with solid organ transplantation.

The invention further concerns a method of prevention or of reducing the risk of blood clotting in an extracorporeal blood circuit during cardiac surgery, or during extracorporeal membrane oxygenation, or during circulatory assistance such as artificial heart, wherein it comprises the administration of the synthetic pentasaccharide compound described here above and salt thereof.

The invention still concerns a kit comprising the synthetic pentasaccharide compound described above and salt thereof or the pharmaceutical composition also described here above and avidin.

DEFINITIONS

The compounds of the present invention may also be present in the form of pharmaceutically acceptable salts. For use in medicine, the salts of the compounds of this invention refer to non-toxic "pharmaceutically acceptable salts." FDA approved pharmaceutically acceptable salt forms include pharmaceutically acceptable acidic/anionic or basic/cationic salts (Gould, P. L., International J. Pharm., 1986, 33, 201-217; Berge, S. M. et al., J. Pharm. Sci., 1977, 66 (1), 1-19).

Pharmaceutically acceptable salts of the acidic or basic compounds of the invention can of course be made by conventional procedures, such as by reacting the free base or acid with at least a stoichiometric amount of the desired salt-forming acid or base.

Pharmaceutically acceptable salts of the acidic compounds of invention include salts with inorganic cations such as sodium, potassium, calcium, magnesium, zinc, ammonium, and salts with organic bases. Suitable organic bases include N-methyl-D-glucamine, arginine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactiobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide. Sulphate salts are particularly preferred.

In the methods of treatment of the present invention, word "administering" shall encompass the treatment of the various described disorders with the specifically disclosed compounds.

It is anticipated that the compounds of the invention can be administered by oral or parenteral routes, including intravenous, intramuscular, intraperitoneal, subcutaneous, transdermal, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate and lactose. Corn starch and alginic acid are suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient is mixed with a solid diluent and soft gelatine capsules wherein the active ingredient is mixed with water or oil such as peanut oil, liquid paraffin or olive oil.

For parenteral use, including intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

Modes of Administration

The compounds of the present invention can be delivered directly or in pharmaceutical compositions containing excipients (see above), as is well known in the art. The present methods of treatment involve administration of a therapeutically effective amount of a compound of the present invention to a subject.

The term "therapeutically effective amount" or "therapeutically effective dose" as used herein refers to an amount of a compound according to the present invention needed to: treat; ameliorate; prevent the targeted disease condition; exhibit a detectable therapeutic or preventative effect; prolong survival of a patient. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The therapeutically effective amount or therapeutically effective dose is the amount of the compound or pharmaceutical composition that will elicit the biological or medical response of a tissue, system, animal, or human that is being sought by the researcher, veterinarian, medical doctor, or other clinician. For example, anticoagulant activity and treatment of blood clotting disorders, e.g., deep vein thromboembolism including deep vein thrombosis and pulmonary embolism, post surgical deep venous thrombosis, coronary syndromes, myocardial infarction, stroke, etc.

The exact formulation, route of administration, dosage, and dosage interval should be chosen according to methods known in the art, in view of the specifics of a patient's condition.

The specific dosage level required for any particular patient will depend on a number of factors, including severity of the condition being treated, the route of administration, the general health of the patient (i.e. age, weight and diet), the gender of the patient, the time and frequency of administration, judgement of the prescribing physician and tolerance/response to therapy. In general, however, the daily dose (whether administered as a single dose or as divided doses) will be in the range 0.01 to 500 mg per day, more usually from 0.1 to 50 mg per day, and most usually from 1 to 10 mg per day. Alternatively, dosages can be administered per unit body weight and, in this instance, a typical dose will be between 0.001 mg/kg and 3 mg/kg, especially between 0.01 mg/kg and 0.2 mg/kg, between 0.02 mg/kg and 0.1 mg/kg.

Chemical Definitions

In the interests of simplicity, terms which are normally used to refer to monovalent groups (such as "alkyl") are also used herein to refer to divalent, trivalent or tetravalent bridging groups which are formed from the corresponding monovalent group by the loss of one or more hydrogen atom(s). Whether such a term refers to a monovalent group or to a polyvalent group will be clear from the context. Where a polyvalent bridging group is formed from a cyclic moiety, the linking bonds may be on any suitable ring atom, according to the normal rules of valency.

As used herein, the term "alkyl" refers to a straight or branched saturated monovalent hydrocarbon radical, having the number of carbon atoms as indicated. For example, the term "(C1-5)alkyl" includes C1, C2, C3, C4 and C5 alkyl groups. By way of non-limiting example, suitable alkyl groups include methyl (-Me), ethyl (-Et), propyl (-Pr), iso-propyl, butyl (-Bu), iso-butyl, tert-butyl, pentyl (-Pent).

Alkoxy refers to the group "alkyl-O—", where alkyl is as defined above. By way of non-limiting example, suitable alkoxy groups include methoxy, ethoxy, propoxy and iso-propoxy.

It will be understood that the invention comprehends the different diastereomers in isolation from each other as well as mixtures.

The counter-ions, which compensate the charged forms of the compounds of the present invention, are pharmaceutically acceptable counter-ions such as hydrogen, or more preferably alkali or alkali-earth metals ions, which include sodium, calcium, magnesium and potassium.

Other 'compound' group definitions will be readily understandable by the skilled person based on the previous definitions and the usual conventions of nomenclature.

It will be appreciated that any optional feature that has been described above in relation to any one aspect of the invention may also be applicable to any other aspect of the invention.

In the description of exemplified compounds, "$IC_{50}$" represents the anti-factor Xa activity.

Applications compounds described here above can be used as a medicament. More in particular, they can be used as medicament intended for the treatment of a blood clotting disorder.

Blood clotting disorder are, in particular, one of venous thrombosis or arterial thrombosis, including deep vein thrombosis, pulmonary embolism, acute coronary syndromes, myocardial infarction and stroke. Blood clotting disorders may also result from atrial fibrillation.

The compound can also be used during ECC (Extracorporeal blood circuit).

Therefore, it is important that the anticoagulant effect can be inhibited or suppressed.

The compound can still be used as a medicament for preventing ischaemia (inadequate blood supply due to blockage of blood vessels) reperfusion injury associated with solid organ transplantation.

The invention is further illustrated by the following examples.

Abbreviations Used

DMF: N,N-Dimethylformamide;
DCM: dichloromethane;
EtOAc: ethyl acetate;
THF: tetrahydrofurane;
MTBE: methyl-tert-butylether;
TFA: trifluoroacetic acid;
TfOH: triflic acid;
$Ac_2O$: acetic anhydride;
Bn: benzyl;
Ph: phenyl;
Bz: benzoyl;
Me: methyl, Et: ethyl, Pr: propyl, Bu: n-butyl, Pent: pentyl, Hex: hexyl; and
Ac: acetate.

Section 1: Synthesis of Monosaccharide D Unit

Scheme 1.

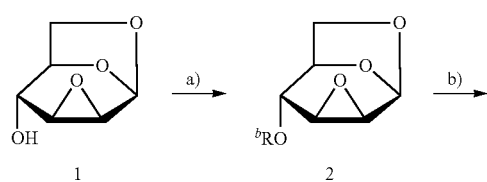

a) $R^b$—X, NaH, DMF; b) $NaN_3$, $NH_4Cl$, $H_2O/(CH_3)_2CH$—OH;
c) $R^a$—X, NaH, DMF, d)$Ac_2O$, TFA; e) HSPhCl, $BF_3 \cdot OEt_2$, Toluene; f) 1N NaOH, $THF/CH_3OH$; g) p-$CH_3OBzCl$, Pyridine.

Preparation of Compound 3

The compound 1,6 and 2,3-dianhydro-4-$OR^b$-[beta]-D-mannopyranose 2 was synthesized from Cerny Epoxide 1 in a similar manner as described by Brill and Tirefort in Tetrahedron Lett. (1998), 39, pp. 787-790. Compound 2 (17.5 mmol) was dissolved in 130 ml of an N,N-dimethylformamide/water mixture [4/1 (v/v)] and sodium azide (22.8 g, 350 mmol) was then added. The reaction medium was heated at 100° C. for 6 hours. After filtering through Celite, the filtrate was diluted with ethyl acetate and then washed with water. The organic phase was dried over sodium sulfate, filtered and then concentrated under vacuum. The residue was recrystallized from an ethyl acetate/cyclohexane mixture (20 ml/7 ml) to afford compound 3 in the form of crystals.

Preparation of Compound 4

To a cooled (0° C.) mixture of compound 3 (11 mmoL) and $R^a$—X (33 mmoL) in anhydrous N,N-dimethylformamide (80 ml) was added portion-wise sodium hydride (1.3 g, 33 mmoL) under an argon atmosphere. The mixture was stirred for 20 hours at room temperature. The excess sodium hydride was destroyed with methanol. The reaction mixture was concentrated under vacuum and the residue was taken up in EtOAc. The organic phase was washed with water, dried over sodium sulfate, filtered and then concentrated under vacuum. The crude material was purified by chromatography on a column of silica gel (n-heptane/EtOAc) to afford compound 4 in the form of a white solid.

Preparation of Compound 5: General Method for Acetolysis

In a dry round-bottom flask, compound 4 (11 mmoL) was dissolved in a mixture of acetic anhydride (73 mL, 770 mmoL, 70 eq.) and trifluoroacetic acid (12.3 mL, 165 mmoL, 15 eq.) at 0° C. The reaction mixture was stirred overnight at room temperature and solvents were removed under reduced pressure followed by co-evaporation with toluene. The residue was purified by flash chromatography on silica gel column to give the desired compound 5 or directly used in the next step without any further purification after washing with a saturated aqueous solution of $NaHCO_3$.

Preparation of Compound 6: Introduction of the Anomeric p-Chlorothiophenol Group $BF_3.OEt_2$ (4.19 mL, 33 mmoL) was added to a stirred suspension of compound 5 (11 mmoL) and 4-p-chlorothiophenol (4.8 g, 33 mmoL) in toluene (55 mL) at 0° C. and the mixture was stirred at room temperature for 7 hours. Saturated solution of $NaHCO_3$ was added until pH=7 and the reaction mixture cooled at −20° C. overnight. The organic layer was separated, diluted with EtOAc and washed with water. The organic layer was dried over $MgSO_4$, the solvent was removed under vacuum and the residue was purified by column chromatography (n-heptane/ethyl acetate) to afford compound 6.

NMR data for two compounds 6f ($R^a$=OEt, $R^b$=OBn) and 6h ($R^a$=OEt, $R^b$=OEt) are described hereunder.

Compound 6f. $^1$H NMR (400 MHz, $CDCl_3$, ppm) δ 7.77-7.41 (m, 10H arom.), 5.73 (d, 1H, J=5.46 Hz, H-1α), 5.14-5.02 (m, 2H, $CH_2$—Bn), 4.56 (d, 1H, J=9.5 Hz, H-1β), 4.48-4.45 (m, 2H, H-6a/b), 4.08-3.82 (m, 2H, R—$CH_2$—$CH_3$), 4.06-3.94 (m, 2H, H-2, H-3), 3.55-3.51 (m, 2H, H-4, H-5), 2.25 (s, 3H, $CH_3$—Ac), 1.42 (t, 3H, J=7.1 Hz, R—$CH_2$—$CH_3$).

Compound 6h. $^1$H NMR (400 MHz, $CDCl_3$, ppm) δ 7.45-7.40 (m, 2H arom.), 7.30-7.27 (m, 2H arom.), 5.48 (d, 1H, J=5.2 Hz, H-1), 4.30-4.26 (m, 2H, H-6a/b), 3.81 (dd, 1H, J=5.2 Hz, J=10.3 Hz, H-2), 3.72, 3.57 (2s, 6H, 2×OMe), 3.50 (t, 1H, J=10.3 Hz, H-3), 2.08 (s, 3H, $CH_3$—Ac).

Preparation of Compound 7: Saponification of the 6-OAc Group

1N Sodium hydroxide (120 mL) was added drop-wise to a solution of compound 6 (120.9 mmoL) in 450 mL THF/methanol (2/1) at 0° C. under stirring. The reaction mixture was stirred for 3 hours at room temperature and then concentrated under vacuum. The residue was dissolved in water and extracted with EtOAc. The organic layer was dried over $MgSO_4$ and the solvent was evaporated to afford compound 7 which was used directly in the next step without any further purification.

Preparation of Compound 8: Introduction of the 6-(p-Methoxybenzoyl-Group)

p-Anisoyl chloride (0.635 g, 3.72 mmoL) was added drop-wise to a stirred solution of compound 7 (3.1 mmoL) in pyridine (10 mL) at 0° C. The reaction mixture was stirred for 3 h at room temperature. The reaction mixture was diluted with DCM (20 mL), washed with 1N HCl (10 mL), dried over $MgSO_4$ and concentrated in vacuo to give crude material 8. Purification by column chromatography (n-heptane/ethyl acetate) afforded pure compound 8 in a good yield as a white solid.

8

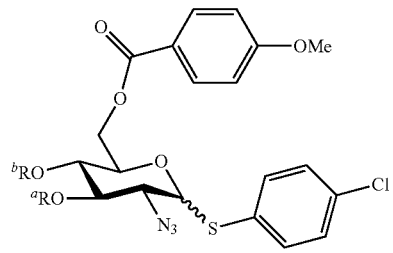

| | compound | | | | | |
|---|---|---|---|---|---|---|
| | 8a | 8b | 8c | 8d | 8e | 8f |
| $OR^a$ | OBn | OBn | OBn | OBn | OMe | OEt |
| $OR^b$ | OBn | OMe | OEt | OPr | OBn | OBn |
| | compound | | | | | |
| | 8g | 8h | 8i | 8j | 8k | 8l |
| $OR^a$ | OMe | OEt | OPr | OBu | OPent | OPr |
| $OR^b$ | OMe | OEt | OPr | OBu | OPent | OBn |

Twelve compounds (8a to 8l) have been prepared and NMR data of some examples are described hereunder.

Compound 8a. $^1$H NMR (400 MHz, $CDCl_3$, ppm) δ 7.83-7.77 (m, 2H arom.), 7.36-7.16 (, m, 12H arom.), 7.09-7.03 (m, 2H arom.), 6.86-6.80 (m, 2H arom.), 5.51 (d, 1H, J=5.3 Hz, H-1α), 4.92-4.74 (m, 4H, 2×$CH_2$—Bn), 4.31 (d, 1H, J=9.8 Hz, H-1β), 3.93-3.85 (m, 1H, H-2), 3.84-3.70 (m, 3H, H-3, H-4, H-5) 3.79 (s, 3H, OMe).

Compound 8f. $^1$H NMR (400 MHz, $CDCl_3$, ppm) δ 8.13-8.08 (m, 2H arom.) 7.69-7.51 (m, 7H arom.), 7.38-7.33 (m, 2H arom.), 7.15-7.09 (m, 2H arom.), 5.79 (d, 1H, J=5.46 Hz, 0.79H-1α), 5.15-5.05 (m, 2H, $CH_2$—Bn), 4.79-4.65 (m, 2H, H-6a/b), 4.58 ( d, 1H, J=9.5 Hz, 0.21H-1β), 4.12-3.87 (m, 2H, R—$CH_2$—$CH_3$), 4.11-4.01 ( m, 3H, H-2, H-3, H-4), 4.08 (s, 3H, OMe), 3.64-3.58 (m, 1H, H-5), 1.45 (t, 3H, J=7.1 Hz, R—$CH_2$—$CH_3$).

Compound 8g. $^1$H NMR (400 MHz, $CDCl_3$, ppm) δ 8.15-8.06 (m, 2H arom.) 7.70-7.50 (m, 7H arom.), 7.38-7.32 (m, 2H arom.), 7.15-7.09 (m, 2H arom.), 5.15-5.05 (m, 2H, $CH_2$—Bn), 5.80 (d, 1H, J=5.46 Hz, H-1α), 4.56 (m, 1H, H-1β), 4.13-3.99 (m, 2H, H-2, H-3), 3.74-3.70 (m, 3H, H-5, H-4), 4.78-4.57 (m, 2H, H-6a/b), 4.03-3.71 (m, 2H, R—$CH_2$—$CH_2$—$CH_3$), 1.92-1.76 (m, 2H, R—$CH_2$—$CH_2$—$CH_3$), 1.12 (t, 3H, J=7.1 Hz, R—$CH_2$—$CH_2$—$CH_3$).

Compound 8h. $^1$H NMR (400 MHz, $CDCl_3$, ppm) δ 7.94-7.90 (m, 2H arom.), 7.41-7.38 (m, 2H arom.), 7.17-7.14 (m, 2H arom.), 6.96-6.91 (m, 2H arom.), 5.54 (d, 1H, J=5.2 Hz, H-1), 4.56 (m, 2H, H-6a/b), 4.44 (m, 2H, H-4, H-5), 3.84 (dd, 1H, J=5.2 Hz, J=10.3 Hz, H-2), 3.79, 3.75, 3.61 (3s, 9H, 3×OMe), 3.50 (t, 1H, J=10.3 Hz, H-3).

Section 2: Synthesis of Pentasaccharides 13 and 15.

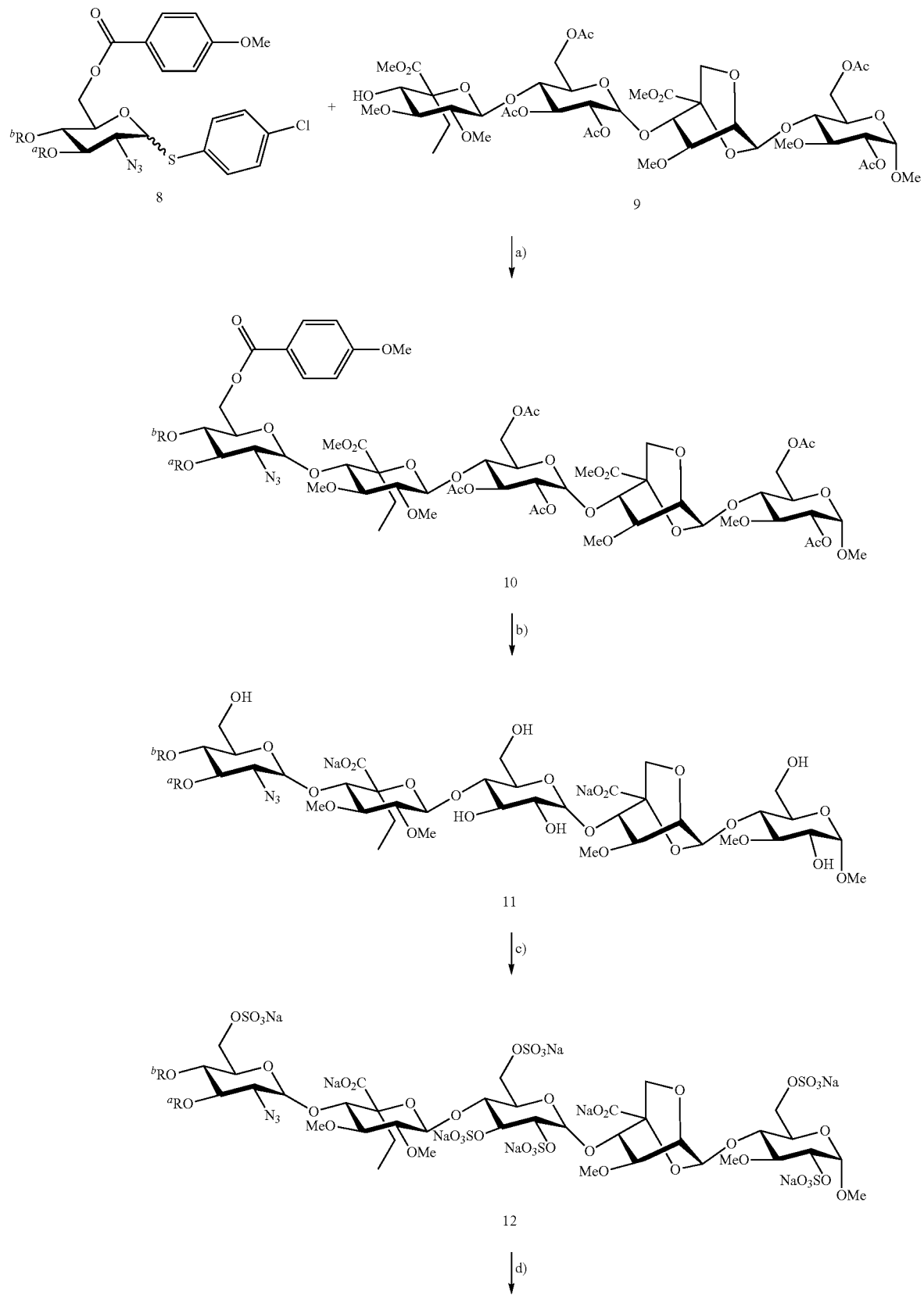
Scheme 2.

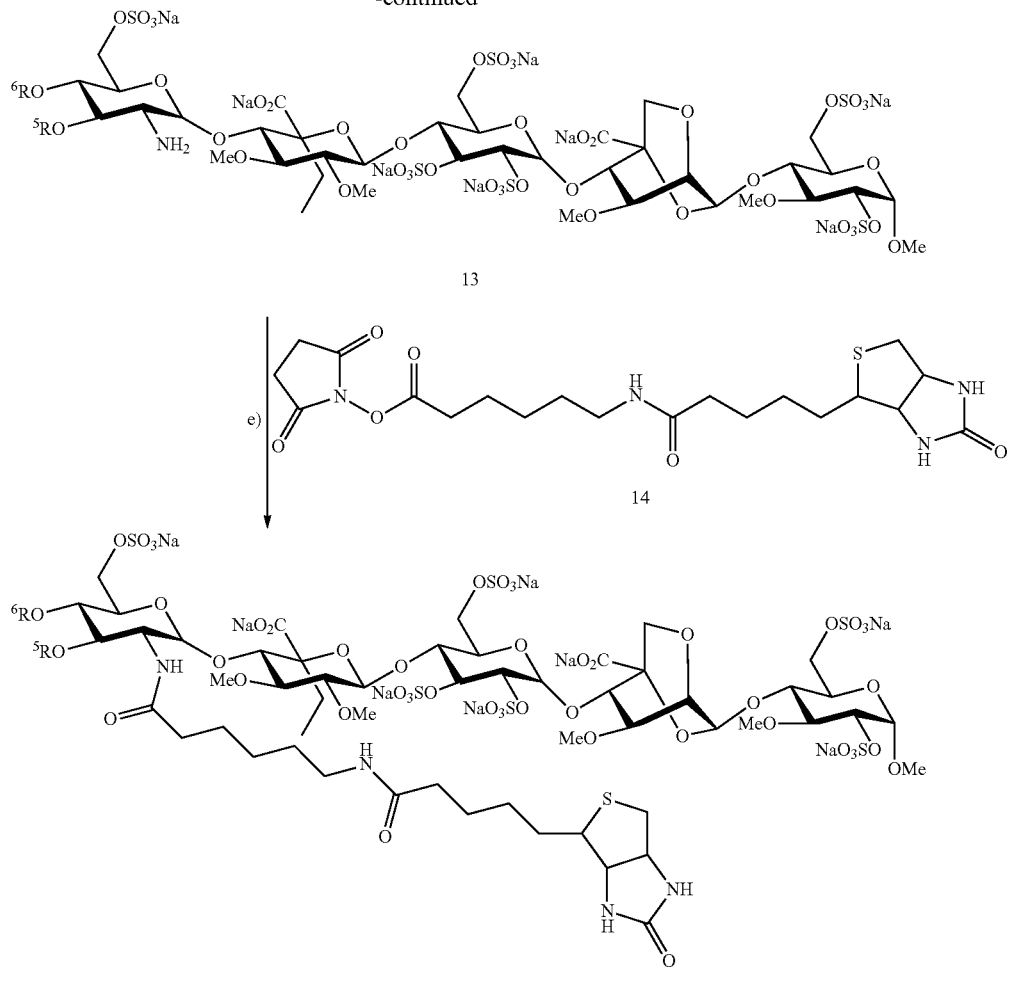

a) TfOH, Bromodan, CH$_2$Cl$_2$/MTBE; b) 2N KOH, CH$_3$OH/THF; c) Py•SO$_3$, pyridine; d) H$_2$, Pd/C, t-BuOH/H$_2$O; e) iPr$_2$NEt, DMF.

Preparation of Compound 10: Glycosidation Step

Tetrasaccharide 9 (9.59 mmol), which was described previously in WO2008/041131, and monosaccharide 8 (19.2 mmol, 2 equiv.) prepared above were dissolved in a 1/3 (v/v) dichloromethane/methyl-tert-butyl ether mixture (267 mL). After addition of 4 A molecular sieve powder (1 weight equivalent/tetrasaccharide 9), the suspension was stirred at room temperature for 2 hour. The mixture was cooled at −50° C., bromodan (28.77 mmol, 3 equiv.) followed by triflic acid (13.43 mmol, 1.4 equiv.) were added and the reaction mixture was stirred for 2 h at −50° C. Further amount of monosaccharide 8 (1 equiv.) was added and the reaction mixture was stirred for 1 h at −50° C. and stored at −20° C. overnight. The reaction mixture was then neutralized by addition of triethylamine to pH 7-8, concentrated under vacuum and the residue was purified by chromatography on silica gel column (toluene/acetone: 90/10 to 80/20) to afford pentasaccharide 10 in 60 to 84% yield.

Preparation of Compound 11: Deacetylation a Saponification 2M aqueous potassium hydroxide solution (6.2 mL) was added at 0° C. to a solution of compound 10 (0.14 mmol) in a 2/1 (v/v) tetrahydrofuran/methanol (15 mL) and the mixture was stirred overnight at room temperature. The reaction mixture was then neutralized with acidic resin Dowex 50x8-100 until pH 4. The resin was removed by filtration and the filtrate was concentrated to dryness under vacuum to afford compound 11 in a quantitative yield.

Preparation of Compound 12: Sulfatation

The sulphur trioxide-pyridine complex (4.2 mmol, 30 equiv.) was added to a solution of compound 11 (0.14 mmol) in anhydrous pyridine (3 mL). The mixture was heated at 80° C. for 16 h with light excluded. After cooling to 0° C., methanol (2 mL) was added and the solution was stirred for 1 hour. An aqueous 5% NaHCO$_3$ solution was then added until pH 7-8 and the mixture was stirred at room temperature overnight and concentrated to dryness. The residue was dissolved in water and desalted on a Sephadex G-25 column eluted with water to afford compound 12 in a 70 to 80% yield.

Preparation of Compound 13: Hydrogenolysis

A solution of compound 12 (0.16 mmol) in a tert-butanol (8 mL)/water (8 mL) mixture was treated under hydrogen atmospheric pressure in the presence of 10% palladium-on-charcoal (1 weight equivalent) for 16 h. After filtering (Millipore(R) LSWP 5 [mu]m filter), the solution was concentrated to dryness to give compound 13 in a quantitative yield.

Compound 13a (OR$^5$=OH, OR$^6$=OH): [α]$_D$=+52.4 (c=0.82, H$_2$O); Mass (ESI method, negative mode); m/z 480.6 [M-3H]$^{3-}$. $^1$H NMR (400 MHz, D$_2$O, ppm) δ 5.64 (d, 1H, J=3.7 Hz, H-1 Glc$^{III}$), 5.43 (s, 1H, H-1 IdoUA$^{II}$), 5.21-5.19 (m, 2H, H-1 Glc$^{I}$, H-1 Glc$^{V}$), 5.07 (d, 1H, J=7.8 Hz, H-1 GlcUA$^{IV}$), 3.75-3.57 (5s, 15H, 5×OMe), 2.26/1.87 (m, 2H, R—CH$_2$—CH$_3$), 1.06 (t, 3H, J=6.9 Hz, R—CH$_2$—CH$_3$).

Compound 13b (OR$^5$=OH, OR$^6$=OMe): Mass (ESI method, negative mode); 922.8055 [M+3DBA-5H]$^{2-}$, 857.7206 [M+2DBA-4H]$^{2-}$, 793.1449 [M+DBA-3H]$^{2-}$, 528.4258 [M+DBA-4H]$^{3-}$, 485.3701 [M-3H]$^{3-}$.

Compound 13c (OR$^5$=OH, OR$^6$=OEt): Mass (ESI method, negative mode); m/z 929.8 [M+3DBA-5H]$^{2-}$, 864.7 [M+2DBA-4H]$^{2-}$, 760.2 [M-2H]$^{2-}$, 490.0 [M-3H]$^{3-}$. $^1$H NMR (400 MHz, D$_2$O, ppm) δ 5.49 (d, 1H, J=3.7 Hz, H-1 Glc$^{III}$), 5.28 (d, 1H, J=1.4 Hz, H-1 ManUA$^{II}$), 5.21 (d, 1H, J=3.4 Hz, H-1 Glc$^{V}$), 5.07 (d, 1H, J=3.7 Hz, H-1 Glc$^{I}$), 4.84 (d, 1H, J=7.4 Hz, H-1 Glc$^{IV}$), 3.93-3.74 (m, 2H, R—CH$_2$—CH$_3$), 3.60, 3.53, 3.45, 3.44, 3.42 (5s, 15H, 5×OMe), 2.07/1.71 (m, 2H, —CH$_2$—CH$_3$), 1.19 (t, 3H, J=6.9 Hz, R—CH$_2$—CH$_3$), 0.90 (t, 3H, J=7.2 Hz, —CH$_2$—OH$_3$).

Compound 13d (OR$^5$=OH, OR$^6$=OPr): Mass (ESI method, negative mode); m/z 872.1984 [M+2DBA-4H]$^{2-}$, 807.6226 [M+1DBA-3H]$^{2-}$, 767.6424 [M-2H]$^{2-}$.

Compound 13e (OR$^5$=OMe, OR$^6$=OH): Mass (ESI method, negative mode); m/z 857.66 [M+2DBA-4H]$^{2-}$, 793.09 [M+1DBA-3H]$^{2-}$, 486.10 [M-3H]$^{3-}$.

Compound 13f (OR$^5$=OEt, OR$^6$=OH): Mass (ESI method, negative mode); m/z 929.3 [M+3DBA-5H]$^{2-}$, 864.7 [M+2DBA-4H]$^{2-}$, 800.1 [M+DBA-3H]$^{2-}$, 760.2 [M-2H]$^{2-}$, 490.0 [M-3H]$^{3-}$.

Compound 13g (OR$^5$=OPr, OR$^6$=OH): Mass (ESI method, negative mode); m/z 871.6919 [M+2DBA-4H]$^{2-}$, 807.1179 [M+DBA-3H]$^{2-}$, 767.1397 [M-2H]$^{2-}$.

Compound 13h (OR$^5$=OMe, OR$^6$=OMe): [α]$_D$=+71.6 (c=1, H$_2$O); Mass (ESI method, negative mode); m/z 864.6 [M+2DBA-4H]$^{2-}$, 800.0 [M+DBA-3H]$^{2-}$, 533.0 [M+DBA-4H]$^{3-}$, 590.0 [M-3H]$^{3-}$.

Compound 13i (OR$^5$=OEt, OR$^6$=OEt): [α]$_D$=+79.3 (c=1, H$_2$O); Mass (ESI method, negative mode); m/z 943.3 [M+3DBA-5H]$^{2-}$, 878.7 [M+2DBA-4H]$^{2-}$, 814.2 [M+DBA+3H]$^{2-}$.

Compound 13j (OR$^5$=OPr, OR$^6$=OPr): [α]$_D$=+64.5 (c=1, H$_2$O); Mass (ESI method, negative mode); m/z 508.7 [M-3H]$^{3-}$.

Compound 13k (OR$^5$=OBu, OR$^6$=OBu): Mass (ESI method, negative mode); m/z 906.6991 [M+2DBA-4H]$^{2-}$, 561.0756 [M+DBA-4H]$^{3-}$, 518.0267 [M-3H]$^{3-}$.

Compound 13l (OR$^5$=OPent, OR$^6$=OPent): [α]$_D$=+66.9 (c=1, H$_2$O); Mass (ESI method, negative mode); m/z 985.3 [M+3DBA-5H]$^{2-}$, 920.8 [M+2DBA-4H]$^{2-}$, 570.4 [M+DBA-4H]$^{3-}$, 527.4 [M-3H]$^{3-}$.

Preparation of Compound 15: LC-Biotinylation

To a solution of compound 13 (0.086 mmol) in anhydrous DMF (8 mL), succinimidyl 6-(biotinamido)hexanoate 14 (58.6 mg, 0.129 mmol) and diisopropylethylamine (22.5 μL, 0.129 mmol) were added and the mixture was stirred for 20 h at room temperature. An aqueous 5% NaHCO$_3$ solution was then added (3.6 mL) and the mixture was stirred at room temperature overnight and concentrated to dryness. The residue was dissolved in water and desalted on a Sephadex G-25 column eluted with water to give compound 15 in a 68 to 87% yield.

Compound 15a (OR$^5$=OH, OR$^6$=OH): [α]$_D$=+64.8 (c=1, H$_2$O); Mass (ESI method, negative mode); m/z 1149.9 [M+4DBA-6H]$^{2-}$, 1084.8 [M+3DBA-5H]$^{2-}$, 1020.3 [M+2DBA-4H]$^{2-}$, 679.8 [M+2DBA-5H]$^{3-}$, 636.8 [M+DBA-4H]$^{3-}$. $^1$H NMR (400 MHz, D$_2$O, ppm) δ 5.66 (d, 1H, J=3.5 Hz, H-1 Glc$^{III}$), 5.42 (s, 1H, H-1 ManUA$^{II}$), 5.32 (d, 1H, J=3.6 Hz, H-1 Glc$^{V}$), 5.22 (d, 1H, J=3.8 Hz, H-1 Glc$^{I}$), 5.17 (d, 1H, J=7.4 Hz, H-1 Glc$^{IV}$), 4.54 (m, 1H, H-6 biotin), 4.42 (m, 1H, H-2 biotin), 3.75-3.54 (5s, 15H, 5×OMe), 3.33 (m, 1H, H-1 biotin), 2.99 (dd, 1H, J=5.0 Hz, J=13.2 Hz, H-7a biotin), 2.76 (d, 1H, J=13.2 Hz, H-7b biotin), 2.28/1.93 (m, 2H, R—CH$_2$—CH$_3$), 1.19 (t, 3H, J=6.9 Hz, R—CH$_2$—CH$_3$).

Compound 15b (OR$^5$=OH, OR$^6$=OMe): [α]$_D$=+59.2 (c=1, H$_2$O); Mass (ESI method, negative mode); m/z 1156.9768 [M+4DBA-6H]$^{2-}$, 1092.9164 [M+3DBA-5H]$^{2-}$, 1027.3103 [M+2DBA-4H]$^{2-}$.

Compound 15c (OR$^5$=OH, OR$^6$=OEt): Mass (ESI method, negative mode); m/z 1163.9 [M+4DBA-6H]$^{2-}$, 1098.9 [M+3DBA-5H]$^{2-}$, 1034.3 [M+2DBA-4H]$^{2-}$, 969.7 [M+DBA-3H]$^{2-}$, 689.2 [M+2DBA-5H]$^{3-}$, 646.1 [M+DBA-4H]$^{3-}$. $^1$H NMR (400 MHz, D$_2$O, ppm) δ 5.49 (d, 1H, J=3.5 Hz, H-1 Glc$^{III}$), 5.26 (s, 1H, H-1 ManUA$^{II}$), 5.16 (d, 1H, J=3.6 Hz, H-1 Glc$^{V}$), 5.06 (d, 1H, J=3.8 Hz, H-1 Glc$^{I}$), 5.01 (d, 1H, J=7.4 Hz, H-1Glc$^{IV}$), 4.54 (m, 1H, H-6 biotin), 4.42 (m, 1H, H-2 biotin), 3.98-3.73 (m, 2H, R—CH$_2$—CH$_3$), 3.59, 3.47, 3.44, 3.43, 3.38 (5s, 15H, 5×OMe), 3.33 (m, 1H, H-1 biotin), 2.99 (dd, 1H, J=5.0 Hz, J=13.2 Hz, H-7a biotin), 2.76 (d, 1H, J=13.2 Hz, H-7b biotin), 1.19 (t, 3H, J=6.9 Hz, R—CH$_2$—CH$_3$).

Compound 15e (OR$^5$=OMe, OR$^6$=OH): Mass (ESI method, negative mode); m/z 1156.9 [M+4DBA-6H]$^{2-}$, 1091.9 [M+3DBA-5H]$^{2-}$, 1027.3 [M+2DBA-4H]$^{2-}$, 962.7 [M+DBA-3H]$^{2-}$. $^1$H NMR (400 MHz, D$_2$O, ppm) δ 7.9 (d, 1H, J=9.1 Hz, NH Glc$^{V}$), 5.50 (d, 1H, J=3.5 Hz, H-1 Glc$^{III}$), 5.27 (s, 1H, H-1 ManUA$^{II}$), 5.12 (d, 1H, J=3.6 Hz, H-1 Glc$^{V}$), 5.06 (d, 1H, J=3.8 Hz, H-1 Glc$^{I}$), 5.01 (d, 1H, J=7.4 Hz, H-1 Glc$^{IV}$), 4.59 (m, 1H, H-6 biotin), 4.41 (m, 1H, H-2 biotin), 3.59, 3.55, 3.47, 3.44, 3.43, 3.37 (6s, 18H, 6×OMe), 3.33 (m, 1H, H-1 biotin), 2.99 (dd, 1H, J=5.0 Hz, J=13.2 Hz, H-7a biotin), 2.76 (d, 1H, J=13.2 Hz, H-7b biotin).

Compound 15f (OR$^5$=OEt, OR$^6$=OH): Mass (ESI method, negative mode); m/z 1163.9 [M+4DBA-6H]$^{2-}$, 1098.9 [M+3DBA-5H]$^{2-}$, 1034.3 [M+2DBA-4H]$^{2-}$, 969.7 [M+DBA-3H]$^{2-}$, 745.2 [M+3DBA-6H]$^{3-}$, 646.1 [M+DBA-4H]$^{3-}$.

Compound 15h (OR$^5$=OMe, OR$^6$=OMe): Mass (ESI method, negative mode); m/z 1164.5 [M+4DBA-6H]$^{2-}$.

Compound 15i (OR$^5$=OEt, OR$^6$=OEt): Mass (ESI method, negative mode); m/z 1178.5 [M+4DBA-6H]$^{2-}$, 1048.8 [M+2DBA-4H]$^{2-}$, 984.2 [M+DBA-3H]$^{2-}$, 698.9 [M+2DBA-5H]$^{3-}$, 655.8 [M+DBA-4H]$^{3-}$.

Compound 15j (OR$^5$=OPr, OR$^6$=OPr): [α]$_D$=+47.4 (c=1.6, H$_2$O); Mass (ESI method, negative mode); m/z 707.8 [M+2DBA-5H]$^{3-}$, 664.8 [M+DBA-4H]$^{3-}$, 621.7 [M-3H]$^{3-}$, 466.0 [M-4H]$^{4-}$.

Compound 15k (OR$^5$=OBu, OR$^6$=OBu): [α]$_D$=+56.1 (c=0.95, H$_2$O); Mass (ESI method, negative mode); m/z 1206.4319 [M+4DBA-6H]$^{2-}$, 1141.9298 [M+3DBA-5H]$^{2-}$, 717.5716 [M+2DBA-5H]$^{3-}$, 674.5105 [M+DBA-4H]$^{3-}$, 631.4722 [M-3H]$^{3-}$.

Compound 15l (OR$^5$=OPent, OR$^6$=OPent): [α]$_D$=+64.0 (c=1, H$_2$O); Mass (ESI method, negative mode); m/z 1220.0267 [M+4DBA-6H]$^{2-}$, 1155.4486 [M+3DBA-5H]$^{2-}$, 1090.3690 [M+2DBA-4H]$^{2-}$, 726.5686 [M+2DBA-5H]$^{3-}$, 683.5173 [M+DBA-4H]$^{3-}$, 640.4665 [M-3H]$^{3-}$.

Section 3: Synthesis of Pentasaccharides 17 and 18

Compounds 17 and 18 were prepared in a similar manner as described for compounds 13 and 15 (scheme 2) starting from tetrasaccharide 16 previously described in WO2006/067173 and monosaccharides 8 as depicted in scheme 3 hereunder.

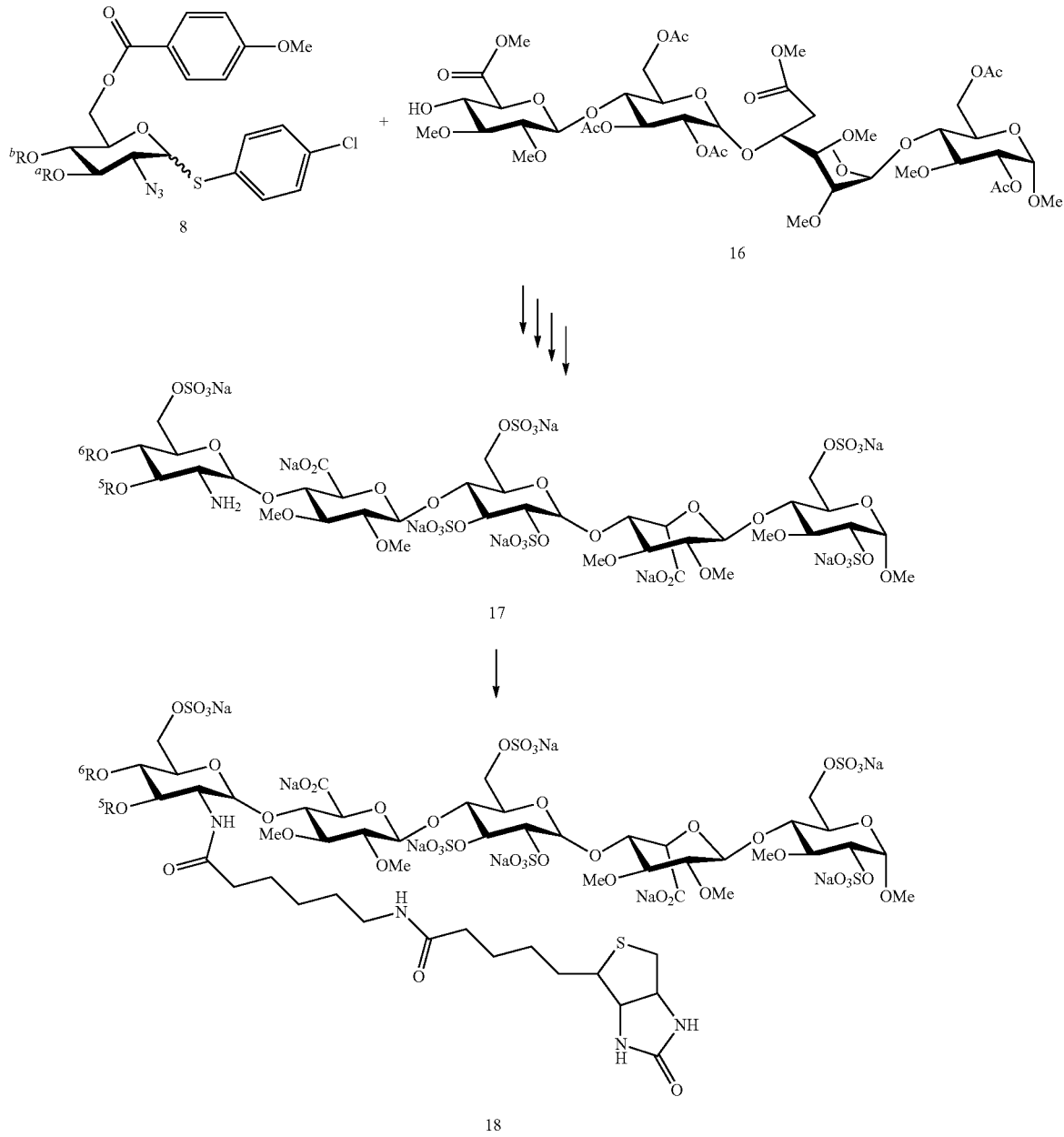

Scheme 3. Synthetic route of compounds 17 and 18 starting from intermediates 8 and 16.

Preparation of compounds 17 was carried out in a similar manner as described for compounds 13.

Compound 17a (OR$^5$=OH, OR$^6$=OH): Mass (ESI method, negative mode); m/z 837.6353 [M+2DBA-4H]$^{2-}$, 773.0602 [M+DBA-3H]$^{2-}$, 708.4929 [M-2H]$^{2-}$. $^1$H NMR (400 MHz, D$_2$O, ppm) δ 5.56 (d, 1H, J=3.4 Hz, H-1 Glc$^V$), 5.51 (d, 1H, J=3.5 Hz, H-1 Glc$^{III}$), 5.20 (d, 1H, J=3.6 Hz, H-1 Glc$^I$), 4.99 (s, 1H, H-1 IdoUA$^{II}$), 4.81 (d, 1H, J=7.8 Hz, H-1 GlcUA$^{IV}$), 3.76-3.57 (6s, 18H, 6×OMe).

Compound 17b (OR$^5$=OH, OR$^6$=OMe): Mass (ESI method, negative mode); m/z 909.2 [M+3DBA-5H]$^{2-}$, 844.7 [M+2DBA-4H]$^{2-}$, 780.1 [M+DBA-3H]$^{2-}$, 715.5 [M-2H]$^{2-}$.

$^1$H NMR (400 MHz, D$_2$O, ppm) δ 5.35 (d, 1H, J=3.6 Hz, H-1 Glc$^{III}$), 5.31 (d, 1H, J=3.5 Hz, H-1 Glc$^V$), 5.04 (d, 1H, J=3.7 Hz, H-1 Glc$^I$), 4.98 (s, 1H, H-1 IdoUA$^{II}$), 4.64 (d, 1H, J=7.8 Hz, H-1 GlcUA$^{IV}$), 3.61 (s, 3H, OMe), 3.55 (2s, 6H, OMe), 3.50 (2s, 6H, OMe), 3.48 (s, 3H, OMe), 3.42 (s, 3H, OMe).

Compound 17c (OR$^5$=OH, OR$^6$=OEt): Mass (ESI method, negative mode); m/z 851.6870 [M+2DBA-4H]$^{2-}$, 787.1106 [M+DBA-3H]$^{2-}$, 722.5338 [M-2H]$^{2-}$, 481.3487 [M-3H]$^{3-}$. $^1$H NMR (400 MHz, D$_2$O, ppm) δ 5.50 (d, 1H, J=3.5 Hz, H-1 Glc$^{III}$), 5.42 (d, 1H, J=3.5 Hz, H-1 Glc$^V$), 5.19 (d, 1H, J=3.8 Hz, H-1 Glc$^I$), 5.13 (s, 1H, H-1 IdoUA$^{II}$), 4.79 (d, 1H, J=7.7 Hz, H-1 GlcUA$^{IV}$), 3.98-3.91 (m, 2H, R—CH$_2$—CH$_3$), 3.75-3.57 (6s, 18H, 6×OMe), 1.32 (t, 3H, J=6.9 Hz, R—CH$_2$—CH$_3$).

Compound 17e (OR$^5$=OMe, OR$^6$=OH): Mass (ESI method, negative mode); m/z 844.6550 [M+2DBA-4H]$^{2-}$, 780.0801 [M+DBA-3H]$^{2-}$, 715.5092 [M-2H]$^{2-}$, 476.6641 [M-3H]$^{3-}$.

Compound 17f (OR$^5$=OEt, OR$^6$=OH): Mass (ESI method, negative mode); m/z 851.7 [M+2DBA-4H]$^{2-}$, 787.1 [M+DBA-3H]$^{2-}$, 722.5 [M-2H]$^{2-}$, 481.3 [M-3H]$^{3-}$.

Compound 17h (OR$^5$=OMe, OR$^6$=OMe): Mass (ESI method, negative mode); m/z 916.2817 [M+3DBA-5H]$^{2-}$, 851.7057 [M+2DBA+2Na-4H]$^{2-}$, 787.1298 [M+DBA-3H]$^{2-}$, 722.5541 [M-2H]$^{2-}$, 481.3654 [M-3H]$^{3-}$. $^1$H NMR (400 MHz, D$_2$O, ppm), δ 5.48 (d, 1H, J=3.5 Hz, H-1 Glc$^V$), 5.36 (d, 1H, J=3.4 Hz, H-1 Glc$^{III}$), 5.04 (m, 2H, H-1 IdoUA$^{II}$, H-1 Glc$^I$), 4.67 (d, 1H, J=7.8 Hz, H-1 GlcUA$^{IV}$), 3.64-3.42 (8s, 24H, 8×OMe).

Preparation of compounds 18 was carried out in a similar manner as described for compounds 15.

Compound 18a (OR$^5$=OH, OR$^6$=OH): Mass (ESI method, negative mode); m/z 718.215 [M+3DBA-6H]$^{3-}$, 671.528 [M+2DBA-5H]$^{3-}$, 628.142 [M+DBA-4H]$^{3-}$, 585.090 [M-3H]$^{3-}$. $^1$H NMR (400 MHz, D$_2$O, ppm) δ 5.35 (d, 1H, J=3.6 Hz, H-1 Glc$^{III}$), 5.29 (d, 1H, J=3.9 Hz, H-1 Glc$^V$), 5.04 (d, 1H, =3.7 Hz, H-1 Glc$^I$), 4.99 (s, 1H, H-1 IdoUA$^{II}$), 4.67 (d, 1H, J=7.8 Hz, H-1 GlcUA$^{IV}$), 3.60-3.42 (6s, 18H, 6×OMe), 4.61 (m, 1H, H-6 biotin), 4.42 (m, 1H, H-2 biotin), 3.33 (m, 1H, H-1 biotin), 3.01 (dd, 1H, J=4.9 Hz, J=13.1 Hz, H-7a biotin), 2.77 (d, 1H, J=13.1 Hz, H-7b biotin).

Compound 18c (OR$^5$=OH, OR$^6$=OEt): Mass (ESI method, negative mode); m/z 1150.8828 [M+4DBA-6H]$^{2-}$, 1086.3187 [M+3DBA-5H]$^{2-}$, 1021.2565 [M+2DBA-4H]$^{2-}$, 956.6723 [M+DBA-3H]$^{2-}$, 892.1098 [M-2H]$^{2-}$, 594.3942 [M-3H]$^{3-}$.

Compound 18e (OR$^5$=OMe, OR$^6$=OH): Mass (ESI method, negative mode); m/z 1143.8594 [M+4DBA-6H]$^{2-}$, 1078.7886 [M+3DBA-5H]$^{2-}$, 1014.2141 [M+2DBA-4H]$^{2-}$, 949.6444 [M+DBA-3H]$^{2-}$, 632.7502 [M+DBA-4H]$^{3-}$, 589.7020 [M-3H]$^{3-}$.

Compound 18f (OR$^5$=OEt, OR$^6$=OH): Mass (ESI method, negative mode); m/z 1151.4 [M+4DBA-6H]$^{2-}$, 1085.8 [M+3DBA-5H]$^{2-}$, 1021.2 [M+2DBA-4H]$^{2-}$, 957.2 [M+DBA-3H]$^{2-}$, 637.4 [M+DBA-4H]$^{3-}$, 594.4 [M-3H]$^{3-}$.

Compound 18h (OR$^5$=OMe, OR$^6$=OMe): Mass (ESI method, negative mode); m/z 637.4261 [M+DBA-4H]$^{3-}$, 594.3792 [M-3H]$^{3-}$, 445.0662 [M-4H]$^{4-}$. $^1$H NMR (400 MHz, D$_2$O, ppm), δ 5.36 (d, 1H, J=3.4 Hz, H-1 Glc$^{III}$), 5.24 (d, 1H, J=3.9 Hz, H-1 Glc$^V$), 5.04 (m, 2H, H-1 Glc$^I$, H-1 IdoUA$^{II}$), 4.66 (d, 1H, J=7.8 Hz, H-1 GlcUA$^{IV}$), 3.59-3.43 (8s, 24H, 8×OMe), 4.59 (m, 1H, H-6 biotin), 4.42 (m, 1H, H-2 biotin), 3.33 (m, 1H, H-1 biotin), 2.99 (dd, 1H, J=4.9 Hz, J=13.1 Hz, H-7a biotin), 2.76 (d, 1H, J=13.1 Hz, H-7b biotin).

Biological Testing

It will be understood that a variety of assays are suitable for testing the biological activity of the compounds of the present invention. However, suitable methods for testing the biological activity of the compounds of the present invention are listed below.

Determination of Anti-Factor Xa Activity of Compounds (IC$_{50}$)

The compounds of the present invention inhibit blood coagulation factor Xa through activation of antithrombin (AT). The compounds were compared as to their ability of inhibiting factor Xa in the presence of AT under standard conditions. For each compound a curve was plotted representing the inhibition % vs. concentration. The concentration inhibiting 50% of the factor Xa activity (IC$_{50}$) was determined. A commercially available system was used for this purpose: compoundStachrom HP kit (Diagnostica Stago). This assay was carried out on a STA Compact (Diagnostica Stago).

Quantification of Compounds in Plasma

Rat plasmatic concentration of compounds (μg compound/mL plasma) was determined using a bioassay based on their anti-factor Xa activity (Stachrom HP kit, Diagnostica Stago as described above). This assay was carried out on a STA Compact (Diagnostica Stago). A specific calibration curve was preformed with each compound to be quantified in rat plasma.

Pharmacokinetic Study after Intravenous Administration (Half-Life of Elimination, T½)

The pharmacokinetics of the compounds of the present invention were investigated in female Wistar Han rats after intravenous administration.

Blood samples were taken at various time points and blood (9 volumes) was mixed with sodium citrate (1 volume) and cooled immediately on ice. The sample was subjected to a centrifugation at 3000×g for 10 minutes at low temperature (the plasma is typically stable for 24 h at temperature below 8° C.) and stored frozen at −20° C. Concentration of compound (per mL of plasma) was determined by their anti-factor Xa activity using factor Xa activity as described above.

For each compound, the half-life of elimination was calculated from the concentration versus time curve thus obtained.

Results

Family 1 (R$^2$ and R$^7$ Form a Bridge, R$^4$=—NH$_2$, and R$^5$=R$^6$)

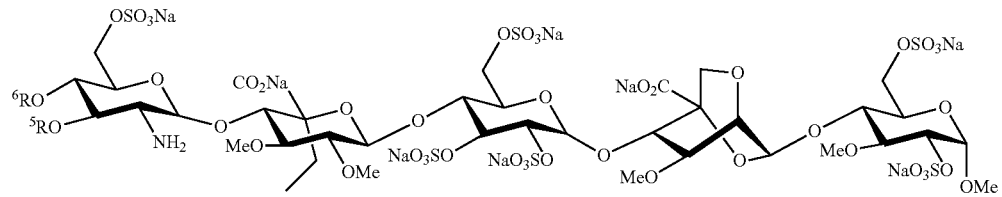

| compound | OR$^5$/OR$^6$ | IC$_{50}$ (nM) | T$_{1/2}$ (h) (Rat) |
|---|---|---|---|
| 13h | —OMe | 99 | 1.2 ± 0.1 |
| 13i | —OEt | 45 | 1.5 ± 0.1 |
| 13j | —OPr | 47 | 1.8 ± 0.1 |
| 13k | —OBu | 34 | 2.2 ± 0.1 |
| 13l | —OPent | 34 | 3.2 ± 0.1 |

Comparison 1

Compound PA01 was synthesized in a similar manner as described by Petitou in WO 99/36428.

(PA01)

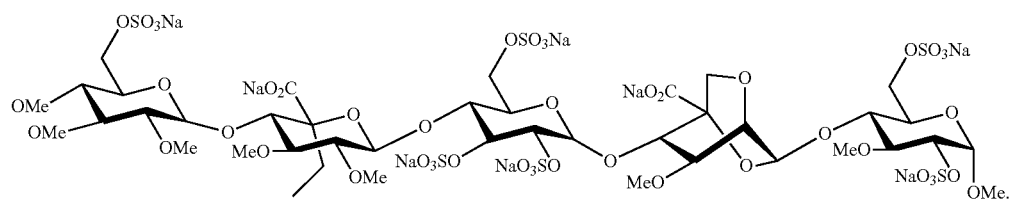

Compound PA01 has a half-life $T_{1/2}$ in rat of 3.5±0.3 h and an $IC_{50}$ activity of 34 nM.

Compound PA01 and compound 13h differ in the $R^4$ group: compound (PA01) having an —OMe group and compound 13h having a —$NH_2$ group. When they are compared, it is observed that the half-life of compound 13h is decreased by about 66% with regards to the half-life of compound PA01.

A comparison can also be made with compounds 13i to 13l. It should be observed that these compounds all have a half-life shorter than that of compound PA01 while their factor Xa inhibitory activity is preserved.

Comparison 2

Compound PA02 was synthesised in a similar manner as described in EP 2 074 131.

| compound | $OR^5/OR^6$ | $IC_{50}$ (nM) | $T_{1/2}$ (h) (Rat) |
|---|---|---|---|
| 13c | —OH/OEt | 84 | 1.4 ± 0.1 |
| 13d | —OH/OPr | 94 | 0.9 ± 0.1 |

It should be again observed that this restricted selection has yielded compounds with short half-lives in comparison with the compounds of the prior art.

Family 3 ($R^2$ and $R^7$ Form a Bridge, $R^4$=—NH-LC-Biotin and $R^5$=$R^6$)

PA02

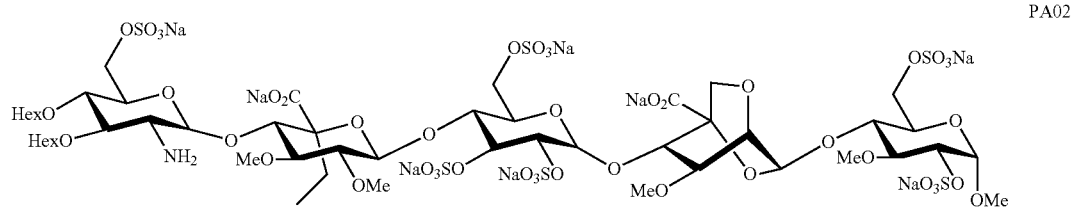

Compound PA02 has a half-life $T_{1/2}$ in rat of 4.8±0.5 and an $IC_{50}$ activity of 108 nM.

Compounds 13h to 13l differ from compound PA02 by having an alkyloxy group in the $R^5$ and $R^6$ with a lower number of carbon atoms. The half-lives in rat of compounds 13h to 13k are shorter than that of compounds PA02, going from 1.2 h (—OMe) to 3.2 h (—OPent).

Furthermore, anti-factor Xa activity of compounds 13h to 13l is increased in comparison with that of compound PA02, i.e. the $IC_{50}$ of compounds 13h to 13k is decreased. The $IC_{50}$ values of compounds 13h to 13l go from 99 nM (—OMe) down to 34 nM (—OBu and —OPent).

It should be noted that this restricted selection has yielded compounds with short half-lives in comparison with the compounds of the prior art.

Family 2 ($R^2$ and $R^7$ Form a Bridge, $R^4$=—$NH_2$ and $R^5 \neq R^6$)

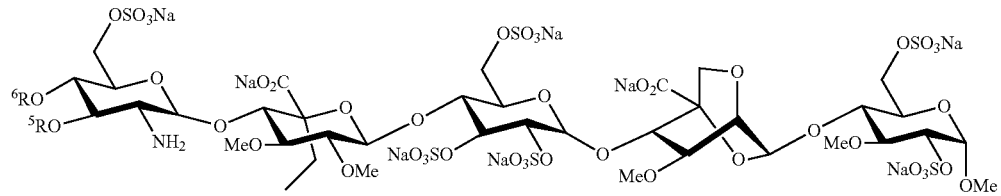

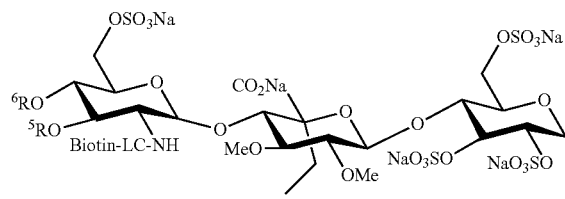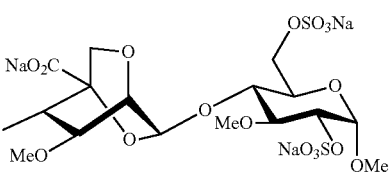

| compound | OR$^5$/OR$^6$ | IC$_{50}$ (nM) | T$_{1/2}$ (h) (Rat) |
|---|---|---|---|
| 15a | —OH | 56 | 1.7 ± 0.2 |
| 15h | —OMe | 32 | 1.6 ± 0.2 |
| 15i | —OEt | 21 | 2.8 ± 0.1 |
| 15k | —OBu | 32 | 3.0 ± 0.2 |

LC represents the following formula:

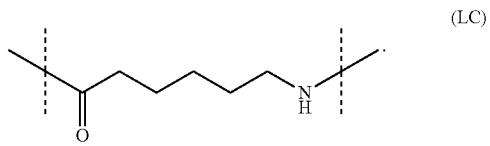

Biotin (or IUPAC name 5-[(3aS,4S,6aR)-2-oxohexahydro-1H-thieno[3,4-d]imidazol-4-yl]pentanoic acid, also known as vitamin B$_7$) represents the following group:

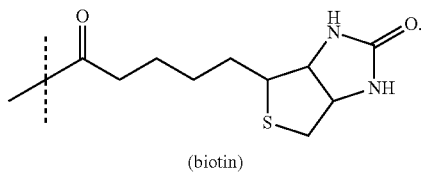

(biotin)

Comparison 3

Compound PA01 and compound 15h differ in the R$^4$ group by compound PA01 having an —OMe group and compound 15h having a —NH-LC-biotin group. When they are compared, it is observed that the half-life of compound 15h is decreased by about 54% with regards to the half-life of compound PA01.

A comparison can also be made with compounds 15a and 15i. It should be observed that these compounds have a half-life shorter than that of compound PA01.

Further, compounds 15h, 15i and 15k, display lower IC$_{50}$ activity and thus are better factor Xa inhibitor than compound PA01.

Comparison 4

Compound PA02 and compound 15a differ in the R$^5$ and R$^6$ groups by compound PA02 having a —OHex (hexoxy) group while compound 15a has a —OH group and in the R$^4$ group by compound PA02 having a —NH$_2$ group while compound 15a has a —NH-LC-biotin group. When both are compared, it is observed that the half-life of compound 15a is decreased by about 73% with regards to compound PA02.

Compounds 15h to 15k differ from compound PA02 by having an alkyloxy group in the R$^5$ and R$^6$ with a lower number of carbon atoms. The half-lives of compounds 15h to 15k are shorter than that of compounds PA02.

Furthermore, activity of compounds 15h to 15k is increased in comparison with that of compound PA02. The IC$_{50}$ value of compound 15a is 56 nM, while those of compounds 15h to 15i remain under 33 nM.

Comparison 5

Compounds of family 1 and of family 3 differ in the R$^4$ group, compounds of Family 1 having a —NH$_2$ group whereas those of Family 3 have a —NH-LC-biotin group. Compounds of Family 3 have a higher anti-factor Xa activity (lower IC$_{50}$) than compounds of Family 1 while still having acceptable half-life values.

Therefore, the grafting of a biotin group on the compounds of Family 1 surprisingly increases the anti-factor Xa activity.

Family 4 (R$^2$ and R$^7$ Form a Bridge, R$^4$=—NH-LC-Biotin and R$^5$≠R$^6$)

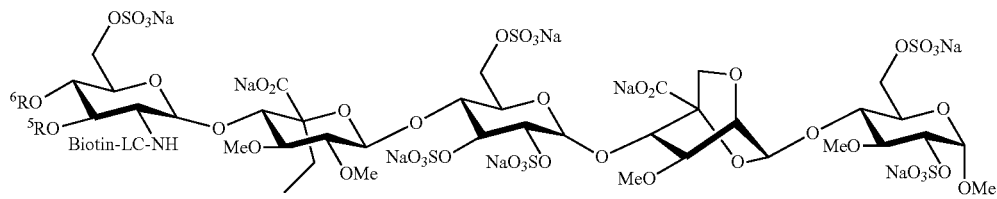

| compound | OR$^5$/OR$^6$ | IC$_{50}$ (nM) | T$_{1/2}$ (h) (Rat) |
|---|---|---|---|
| 15b | —OH/OMe | 42 | 1.3 ± 0.1 |
| 15e | —OMe/OH | 65 | 1.3 ± 0.1 |
| 15c | —OH/OEt | 30 | 2.2 ± 0.2 |
| 15f | —OEt/OH | 50 | 1.3 ± 0.0 |

Comparison 6 compounds of Family 2 and of family 4 differ in the R$^4$ group by compounds of Family 2 having a —NH$_2$ group whereas those of Family 4 have a —NH-LC-biotin group. Compounds of Family 4 have a higher anti-factor Xa activity (lower IC$_{50}$) than compounds of Family 2 while still having acceptable half-life values.

Therefore, the grafting of a biotin group on the compounds of Family 2 surprisingly increases the anti-factor Xa activity.

Family 5 (R² = Alcoxy, R⁷ = H, R⁴ = —NH₂)

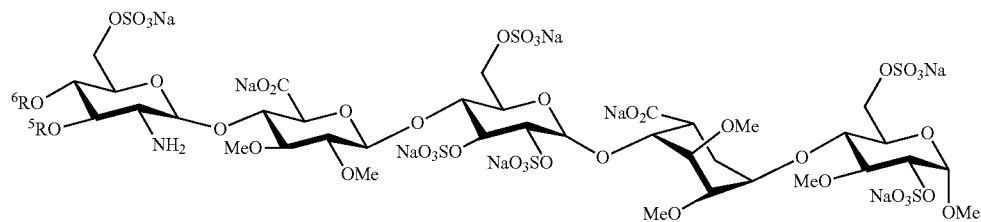

| compound | OR⁵/OR⁶ | IC₅₀ (nM) | T₁/₂ (h) (Rat) |
|---|---|---|---|
| 17h | —OMe/OMe | 59 | 1.2 ± 0.1 |
| 17c | —OH/OEt | 103 | 1.3 ± 0.1 |

Family 6 (R² = Alcoxy, R⁷ = H, R⁴ = —NH-LC-Biotin)

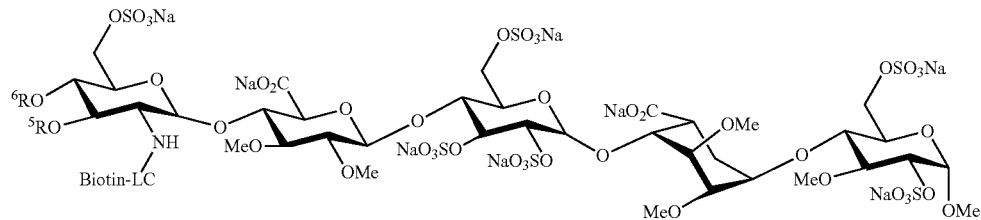

| compound | OR⁵/OR⁶ | IC₅₀ (nM) | T₁/₂ (h) (Rat) |
|---|---|---|---|
| 18a | —OH/OH | 53 | 1.9 ± 0.1 |
| 18b | —OH/OMe | 34 | 2.4 ± 0.1 |
| 18e | —OMe/OH | 55 | 1.5 ± 0.1 |
| 18f | —OEt/OH | 39 | 2.3 ± 0.2 |
| 18c | —OH/OEt | 31 | 1.9 ± 0.2 |

Comparison 7

When comparing corresponding compounds of Family 5 and family 6, which differ in the $R^4$ group, Family 5 has a —NH₂ group whereas those of Family 6 have a —NH-LC-biotin group, the anti-factor Xa activity of the compounds of Family 6 are higher than the anti-factor Xa activity of the compounds of Family 5 while still having acceptable half-life values.

Therefore, the grafting of a biotin group on the compounds of Family 5 surprisingly increases the anti-factor Xa activity.

The invention claimed is:

1. A synthetic pentasaccharide compound of formula (I):

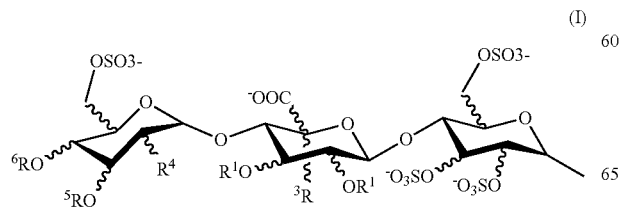

(I)

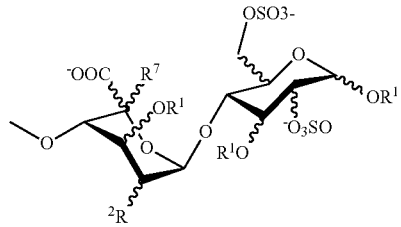

-continued wherein:

$R^1$ represents a (C1-C3)alkyl group;

$R^2$ represents a (C1-C3)alkoxy group and $R^7$ represents a hydrogen atom, or $R^2$ and $R^7$ form a —O—CH₂— or a —O—CH₂—CH₂— bridge, where —O— is linked to the carbon atom bearing the $R^2$ group and —CH₂— is linked to the carbon atom bearing the $R^7$ group;

$R^3$ represents a hydrogen atom or an ethyl group;

$R^4$ represents —NH-LC-biotin, wherein LC represents a linker;

when $R^5$ and $R^6$ are different, $R^5$ and $R^6$ are chosen amidst a hydrogen atom, a methyl, an ethyl, a propyl, a butyl and a pentyl group;

when $R^5$ and $R^6$ are identical, $R^5$ and $R^6$ are chosen amidst a hydrogen atom, a methyl, an ethyl, a propyl and a pentyl group;

on the proviso that $R^1$ differs from at least one of $R^5$ or $R^6$;

or a salt thereof.

2. The synthetic pentasaccharide compound of claim 1 wherein the compound has the following formula (II):

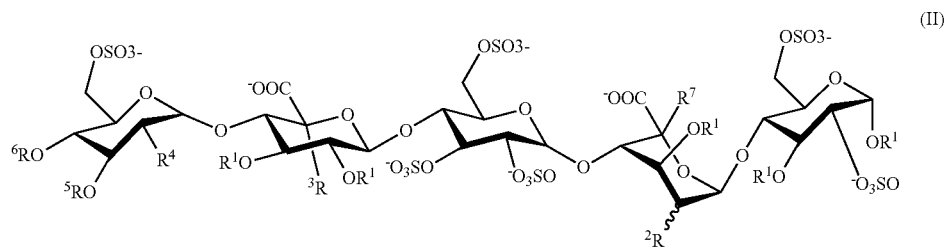

(II)

wherein:

$R^1$, $R^2$, $R^3$, $R^4$, $R^5$ and $R^6$ are defined as in claim 1 or a salt thereof.

3. The synthetic pentasaccharide compound or a salt of claim 1, wherein $R^5$ and $R^6$ represent the same group.

4. The synthetic pentasaccharide compound or a salt of claim 1, wherein one of $R^5$ or $R^6$ represents an hydrogen atom, and the other represents a (C 1-C5)alkyl group.

5. The synthetic pentasaccharide compound or a salt of claim 1, wherein $R^2$ and $R^7$ form a —O—CH$_2$— bridge, where —O— is linked to the carbon atom bearing the $R^2$ group and —CH$_2$— is linked to the carbon atom bearing the $R^7$ group, and $R^3$ represents an ethyl group.

6. The synthetic pentasaccharide compound or a salt of claim 1, wherein $R^2$ represents a (C1-C3)alkoxy group, and $R^3$ and $R^7$ represent a hydrogen atoms.

7. The synthetic pentasaccharide compound or a salt of claim 1 selected from the group consisting of:

compounds 15a, 15b, 15c, 15d, 15e, 15f, 15g, 15h, 15i, 15j, 15l and;

compounds 18a, 18b, 18c, 18d, 18e, 18f, 18g, 18h.

8. A pharmaceutical composition comprising the synthetic pentasaccharide compound or a salt of claim 1 and a pharmaceutically acceptable diluent or carrier.

9. A kit comprising the pharmaceutical composition of claim 8 and avidin.

10. The synthetic pentasaccharide compound or a salt of claim 1, wherein LC represents a linker of the formula —(C=O)—(CH$_2$)$_n$—NH—, with n from 1 to 10.

11. The synthetic pentasaccharide compound and salt of claim 10, wherein LC represents a linker of formula —(C=O)—(CH$_2$)$_4$—NH.

* * * * *